United States Patent [19]

Jacobs et al.

[11] Patent Number: 5,552,177
[45] Date of Patent: Sep. 3, 1996

[54] METHOD FOR APPLYING ADHESIVE TO THE BASE OF AN ORTHODONTIC APPLIANCE

[75] Inventors: Dwight W. Jacobs, River Falls, Wis.; Oliver L. Puttler, La Crescenta, Calif.; Evangelos G. Georgakis, Altaloma, Calif.; Allen B. Amundson, Upland, Calif.; Russell A. Jordan, Rancho Cucamonga, Calif.

[73] Assignee: Minnesota Mining and Manufacturing Company, St. Paul, Minn.

[21] Appl. No.: 407,622

[22] Filed: Mar. 21, 1995

[51] Int. Cl.$^6$ .................. B05D 3/12; B05D 5/10
[52] U.S. Cl. .................. 427/2.29; 427/374.1; 427/398.2; 427/208.2
[58] Field of Search .................. 427/2.29, 398.2, 427/348, 374.1, 208.2, 289, 369

[56] References Cited

U.S. PATENT DOCUMENTS

| 3,154,428 | 10/1964 | Cochrane et al. | 427/374.1 |
|---|---|---|---|
| 3,916,055 | 10/1975 | Wagner | 156/272.4 |
| 4,022,926 | 5/1977 | Keough et al. | 427/265 |
| 4,152,189 | 5/1979 | Guerin | 427/208.2 |
| 4,173,506 | 11/1979 | Pletcher | 427/208.2 |
| 4,242,158 | 12/1980 | Olson | 427/348 |
| 4,961,804 | 10/1990 | Aurichio | 427/208.2 |
| 4,978,007 | 12/1990 | Jacobs et al. | 206/469 |
| 5,015,180 | 5/1991 | Randklev | 433/9 |
| 5,053,254 | 10/1991 | Billeter | 427/348 |
| 5,172,809 | 12/1992 | Jacobs et al. | 206/368 |
| 5,328,363 | 7/1994 | Chester et al. | 433/9 |
| 5,348,154 | 9/1994 | Jacobs et al. | 206/369 |
| 5,350,059 | 9/1994 | Chester et al. | 906/63.5 |
| 5,350,477 | 9/1994 | Chevalier et al. | 427/398.2 |
| 5,354,199 | 10/1994 | Jacobs et al. | 433/9 |

*Primary Examiner*—Diana Dudash
*Attorney, Agent, or Firm*—Gary L. Griswold; Walter N. Kirn; James D. Christoff

[57] ABSTRACT

Orthodontic adhesive is cooled below ambient temperature in order to facilitate applying the adhesive to the base of an orthodontic appliance. The adhesive is placed on a carrier and formed into a certain shape on the carrier, and then released from the carrier while cool. In one embodiment, a quantity of adhesive is placed on the base of the appliance, and the appliance is then moved to a cut-off die while the adhesive remains cool and relatively brittle; next, a stream of pressurized air fractures and removes excess adhesive from the appliance base.

15 Claims, 9 Drawing Sheets

METHOD FOR APPLYING ADHESIVE TO THE BASE OF AN ORTHODONTIC APPLIANCE

BACKGROUND OF THE INVENTION

1. Field of the Invention

The present invention relates to a method for applying an orthodontic adhesive to the base of an orthodontic appliance, and is especially suitable in the manufacture of packaged, adhesive precoated orthodontic appliances.

2. Description of the Related Art

Orthodontic treatment involves movement of malpositioned teeth to orthodontically correct positions. Tiny orthodontic appliances known as brackets are connected to anterior, cuspid and bicuspid teeth, and an archwire is placed in a slot of the brackets. The archwire forms a track to guide movement of the teeth to desired positions for correct occlusion. Often, the ends of the archwire are held by appliances known as buccal tubes that are secured to molar teeth.

In previous years, orthodontic appliances such as brackets and buccal tubes were connected to teeth by welding or brazing each appliance to a band that was then placed over the desired tooth in encircling relation. In more recent years, however, it has become common practice to bond orthodontic brackets directly to the surface of the tooth. Omission of the metal bands long associated with the brackets provides a more aesthetic appearance than the appearance of brackets welded to bands, and helps to alleviate the problem of the "tinsel tooth" or "metallic mouth" appearance that is often associated with orthodontic treatment.

For many years, it was common practice to apply orthodontic adhesive to the base of directly-bonded brackets immediately before the brackets and adhesive were placed on the tooth. In some instances, a quantity of the adhesive would be dispensed onto a mixing pad or dispensing well, and the orthodontist or the orthodontist's staff would then use a small spatula to "butter" each appliance with a small dab of adhesive. In other instances, the orthodontist or the orthodontist's staff would dispense a quantity of adhesive from a syringe onto the bracket base.

Recent advances relating to orthodontic appliances include adhesive precoated brackets such as are described in U.S. Pat. Nos. 4,978,007, 5,015,180 and 5,328,363. Adhesive precoated brackets typically include brackets upon which the manufacturer has applied a precise quantity of adhesive such as a photocurable adhesive. The adhesive is protected from light, evaporation, oxidation, contamination, humidity and sublimation by a release liner or outer package until use. When it is desired to mount the bracket on a tooth, the bracket is released from a release liner or coating (if provided) and then, with the adhesive, is simply placed directly on the tooth.

Adhesive precoated brackets provide a significant advantage to the orthodontist in that the orthodontist or the orthodontist's staff need not carefully dispense the adhesive through a syringe onto the base of each bracket, or alternatively need not dispense the adhesive onto a mixing pad or well and then carefully transfer the adhesive to the base of each bracket. Furthermore, the manufacturer can control the quantity of adhesive placed on each bracket. As a result, there is sufficient adhesive to substantially fill the space between the bracket base and the tooth when the bracket is pushed in position, and yet there is not an inordinate amount of adhesive such that excessive cleanup around the perimeter of the bracket base would be necessary. Advantageously, the adhesive is preferably a light-curable adhesive so that the bracket can be carefully positioned in a proper orientation on the tooth surface before a curing lamp is activated to cure the adhesive and securely fix the bracket in place.

One method of precoating orthodontic brackets with adhesive in automated fashion includes the use of an adhesive syringe that is activated by air pressure. The syringe is inverted and dispenses adhesive in such a manner that the adhesive hangs from the tip of the syringe by gravity. A bracket, carried by a bracket holder, is oriented such that the plane of the base of the bracket is vertical and the bracket moves in a horizontal direction toward a position next to a portion of the adhesive that is hanging from the syringe. Next, a pair of cutters, spaced vertically apart a distance that is approximately the height of the bracket base, are moved toward the bracket base and into the adhesive to cut a section of the adhesive. A blast of pressurized air is simultaneously directed toward the adhesive to push the cut section of the adhesive ribbon onto the base and also to blow the remaining, excess adhesive away from the bracket.

There is a continuing need in the art for improvements in the methods for precoating orthodontic appliances with adhesive. For example, it is desirable to increase the speed of the precoating method so that the manufacturing costs of precoating each appliance can be reduced. However, it is also important for each appliance to receive a precise volume quantity of adhesive to insure that the adhesive firmly affixes the appliance base to the tooth to avoid unintentional separation. It would also be advantageous to provide a precoating method that may be carried out in automated fashion with little, if any, attention by the operator.

SUMMARY OF THE INVENTION

The present invention is directed toward a method for applying adhesive to a base of an orthodontic appliance, and comprises the steps of placing a quantity of adhesive onto a carrier, and cooling at least a portion of the adhesive to a temperature below ambient. The method also includes the steps of contacting the base of the bracket with the adhesive, and disengaging the adhesive from the carrier while the temperature of the portion of the adhesive is below ambient.

It has been observed that cooling at least a portion of the adhesive greatly facilitates automated handling of the adhesive, inasmuch as the cooled adhesive readily releases from the carrier and exhibits handling characteristics similar to a solid material instead of a paste. Lowering the temperature of the adhesive also enhances other operations, such as the step of trimming away excess adhesive to leave a precise quantity on the appliance that is sufficient for bonding the appliance to a tooth.

DETAILED DESCRIPTION OF THE PREFERRED EMBODIMENTS

FIGS. 1–7 illustrate an apparatus 20 for carrying out a method for applying adhesive to a base of an orthodontic appliance in accordance with one embodiment of the invention. An overview of the apparatus 20 may be appreciated by viewing both of the schematic illustrations of FIGS. 1 and 2.

Figure 1:
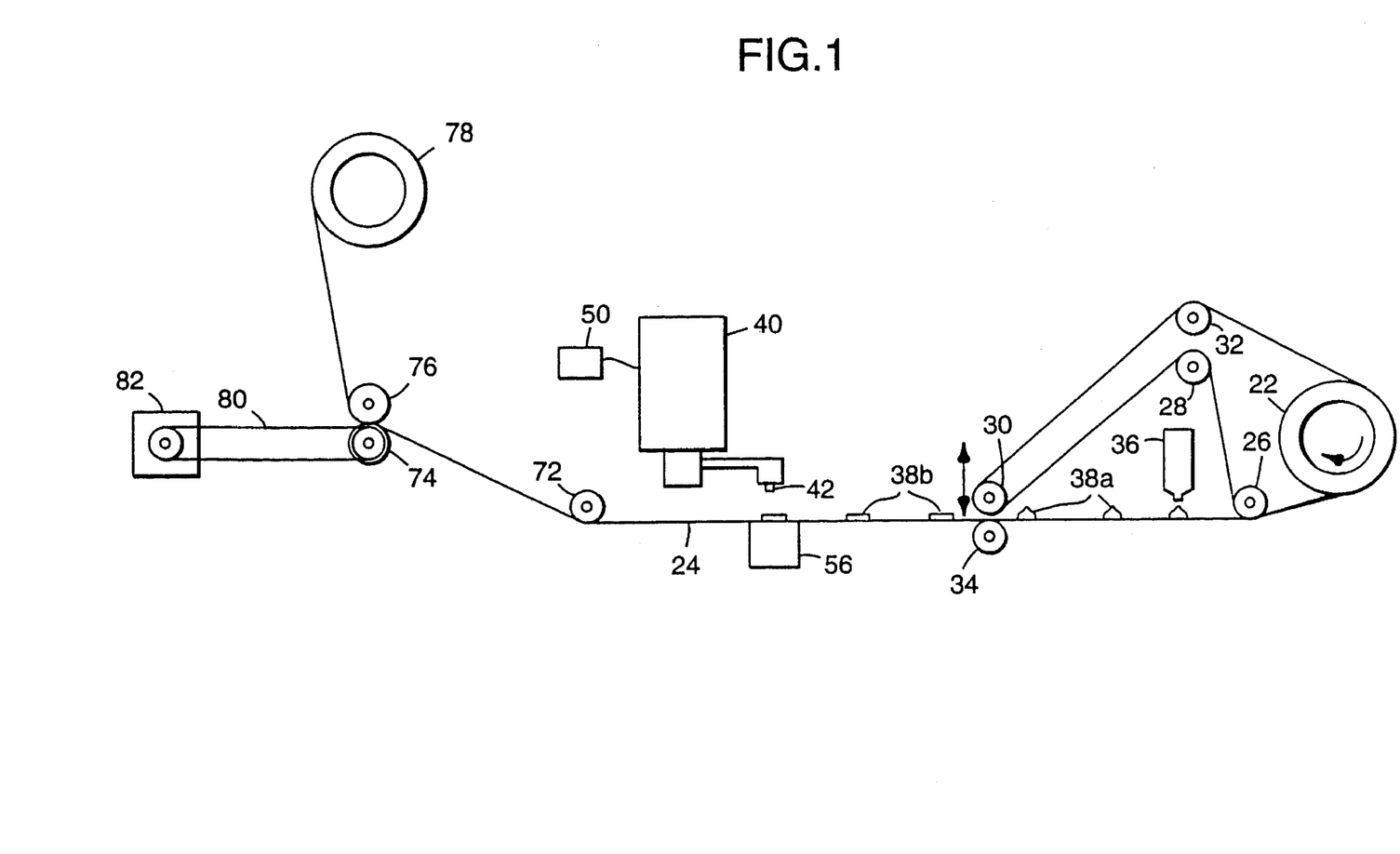
FIG. 1 is a side elevational schematic view of part of an apparatus for carrying out a method of the invention according to one embodiment.

In more detail, the apparatus 20 includes a take-off spool 22. A length of 0.002 in. (0.05 mm) thick polyester carrier 24, in the nature of a flexible carrier strip having an outer surface that readily releases from orthodontic adhesive, is wound about the take-off spool 22. When the carrier 24 is unwound from the take-off spool 22, the carrier 24 first passes beneath a first roller 26, then over a second roller 28, then beneath a third roller 30 and over a fourth roller 32. As is shown in FIG. 1, the carrier 24 then passes around the take-off spool 22, again beneath the first idler roller 26 and then above a fifth roller 34 that is located immediately beneath the third roller 30.

A dispensing unit 36 is located above the path of travel of the carrier 24 as the carrier 24 passes beneath the first roller 26 for the second time and toward the fifth roller 34. The dispensing unit 36 includes a syringe containing an orthodontic adhesive that is preferably photocurable and preferably contains sufficient ethoxylated bisphenol diacrylate or dimethacrylate so that satisfactory storage-stable characteristics are obtained. Suitable adhesives are described in U.S. Pat. No. 5,354,199, which is expressly incorporated by reference herein. A presently preferred adhesive includes the following components (given in weight percent): 11.45% diglycidylmethacrylate of Bisphenol A ("Bis-GMA"; from 3M Company), 7.47% ethoxylated Bisphenol A dimethacrylate ("EBDMA"; DIACRYL 101 from Akzo Chemicals Inc.), 0.06% camphorquinone ("CPQ"; a photoinitiator from Aldrich Chemical Company), 0.15% diphenyliodonium hexafluorophosphate ("$(C_6H_5)_2I^+PF_6^-$"; a catalyst from 3M Company), 0.02% butylated hydroxytoluene ("BHT"; an inhibitor from PMC Specialties), 0.24% ethyl 4-dimethylaminobenzoate ("EDMAB"; an amine from Aldrich Chemical Company), and 80.61% quartz filler (from Orthocast Manufacturing Co.) that is comminuted to a particle surface area of 2.2–2.9 $m^2/g$ and silane-treated with 2.60% gamma-methacryloxypropyl trimethoxysilane (A-174, Union Carbide Corp.) based on the weight of the filler.

The dental adhesive can also contain suitable adjuvants such as solvents, accelerators, absorbers, diluents, stabilizers, pigments, dyes, inorganic or organic fibrous or particulate reinforcing or extending fillers, viscosity modifiers, inhibitors, surface tension depressants, wetting aids, thixotropic agents, antioxidants, medicaments (e.g., leachable fluorides), and other ingredients well known to those skilled in the art.

The viscoelastic behavior of the adhesive is determined by a consistency measurement. Consistency is measured as the spread of 1.04 g±0.01 g of adhesive sandwiched between two 10.16×10.16 cm glass plates under a 907.2 g weight. The adhesive is delivered onto the bottom plate, then the top plate and the 907.2 g weight are gently lowered onto the adhesive. The combined mass of the top plate and the 907.2 g weight is 1027±10 g. After two minutes, the spread (diameter) of the adhesive is measured to the nearest 0.8 mm in three radial directions, and three readings are averaged. The consistency is preferably in the range of about 12 mm to 28 mm, more preferably is in the range of about 21 mm to about 26 mm, and most preferably is in the range of about 23 mm to about 24.5 mm.

The syringe of the dispensing unit 36 is connected to a source of pressurized air. The flow of pressurized air is computer controlled for intermittent dispensing of adhesive on the carrier 24. Optionally, the viscosity of the adhesive may be reduced to facilitate dispensing. One method of reducing the adhesive viscosity is to surround the syringe with a heating element that raises the temperature of the adhesive in the syringe to about 120° F. (49° C.) to enhance dispensing. Another method of reducing the adhesive viscosity is to add a quantity of solvent to the adhesive prior to dispensing, and then to remove the solvent from the adhesive in a secondary operation after dispensing and before forming the adhesive into a disc-like shape. As the carrier 24 advances, the syringe dispenses discrete, spaced apart quantities of adhesive (such as adhesive 38a shown in FIG. 3) having a generally teardrop shape that is flattened on its lower side once in contact with the carrier 24.

As the carrier 24 advances, each droplet of adhesive 38a passes between a nip presented by adjacent stretches of the carrier 24 that are located between the rollers 30, 34. After passing between the rollers 30, 34, the adhesive is flattened to a disc-shaped configuration (as noted by the shape of the adhesive 38b in FIG. 3). As the droplets 38b pass through the nip, the upper stretch of the carrier 24 detaches from the droplets 38b in a peeling fashion to enhance separation of the upper stretch from the droplets 38b. The distance between the rollers 30, 34 is adjusted so that thickness of each quantity of adhesive 38b is approximately 0.025 in. (0.6 mm).

The amount of adhesive dispensed each time from the dispensing unit 36 is in the range of about 30 to 50 mg, or about 0.01 to 0.02 ml when the aforementioned preferred adhesive is used. The precise quantity of adhesive in each droplet 38a is relatively unimportant, however, inasmuch as the rollers 30, 34 flatten the droplets 38a to a uniform, pre-selected thickness. As will be understood in the paragraphs that follow, excess adhesive is trimmed away from the bracket base during subsequent steps.

A computer controlled pick and place device 40, shown schematically in FIG. 1, has a movable arm with a mechanical gripper 42 that is illustrated in FIGS. 3–7. The gripper 42 includes two relatively stationary fingers 46 and two relatively movable fingers 48 having concave outer surfaces for releasably grasping an orthodontic appliance such as a bracket 44 in order to apply adhesive to a tooth-facing base of the bracket 44. The two relatively stationery fingers 46 are spaced apart from each other. The fingers 46 are arranged to enter the occlusal-gingival channel between mesial and distal pairs of tiewings on a twin orthodontic bracket, and are adapted to engage the labial side of the base of the bracket directly adjacent to occlusal and gingival edges of the bracket body that extend labially from the bracket base.

The two relatively movable fingers 48 of the gripper 42 are connected to a common pivot and movable by a pneumatic piston-and-cylinder assembly toward a retracted, adjacent orientation. The relatively movable fingers 48, are also connected to a spring for simultaneous outward movement when the pneumatic pressure is released in order to engage the inner side walls of the aforementioned occlusal-gingival channel between the tiewings of the bracket 44 when the stationary fingers 46 are also in the channel and in contact with the labial side of the bracket base.

Movement of the arm of the pick and place device 40 as well as pressure in the pneumatic piston-and-cylinder assembly connected to the movable fingers 48 are controlled by a master controller 50 (Compumoter, no. 4408). The pick and place device 40 is a four-axis robot (Seiko, no. DTRAN RT 2000) that is controlled for movement by an internal controller that, in turn, is operatively connected to the master controller 50. However, as can be understood by those skilled in the art, the pick and place device 40 can instead be a relatively inexpensive two-axis robot having a read only memory.

The computer is programmed to move the gripper 42 to a location directly over a vibratory feeding track 52 having a supply of the brackets 44. The feeding track 52 is inclined and includes an elongated upwardly facing channel that carries an aligned row of brackets in an orientation wherein the base of the bracket faces downwardly. As the track vibrates, the brackets 44 in the channel of the feeding track 52 move toward a common pick-up location that is designated by the numeral 54 in FIG. 2.

A freezing probe 56 is centrally located beneath the path of travel of the carrier 24 downstream of the rollers 30, 34. The freezing probe 56 (Neslab "R" probe) comprises a cylindrical, metallic, thermally conductive block that is surrounded by a refrigerant coil connected to a temperature controlled refrigeration unit (Neslab Cryocool immersion cooler, no. CC-100 II).

Figure 3:
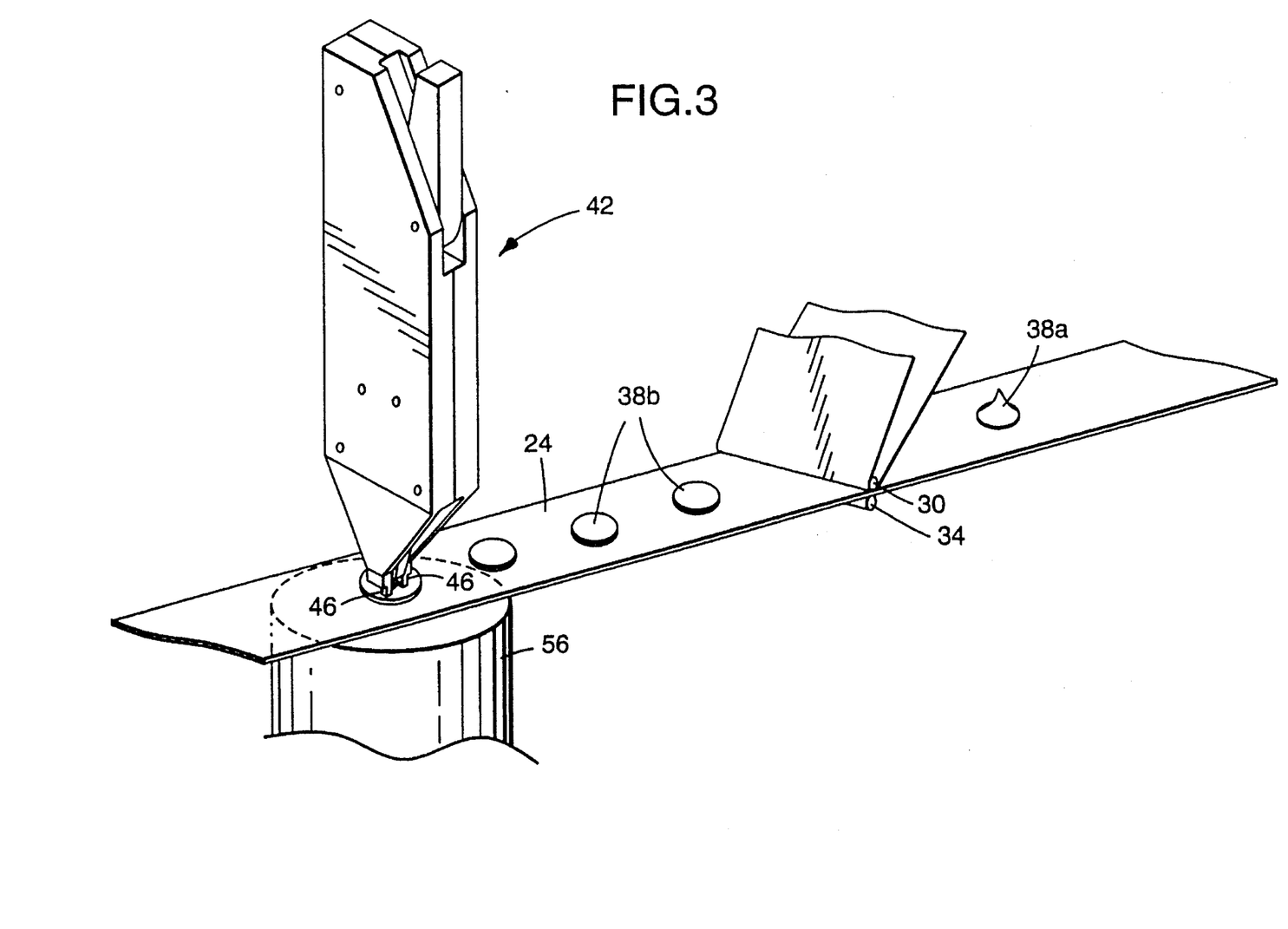
FIG. 3 is an enlarged, perspective, fragmentary view of a portion of the apparatus shown in FIGS. 1–2, wherein discrete quantities of adhesive are flattened while advanced by a carrier toward a freezing probe.
Figure 4:
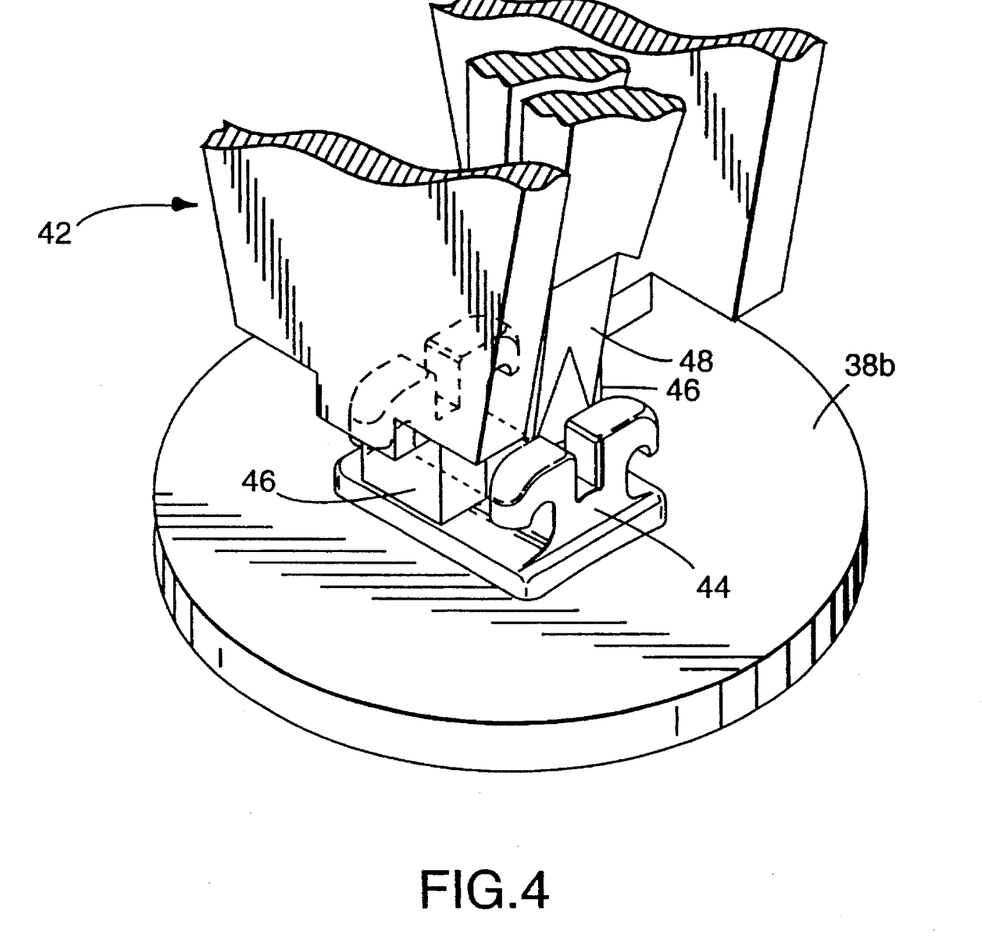
FIG. 4 is an enlarged, perspective, fragmentary view of part of the apparatus illustrated in FIG. 3, and particularly showing a gripper of a pick and place device that has moved an orthodontic bracket into contact with adhesive while the adhesive is located over the freezing probe.
Figure 5:
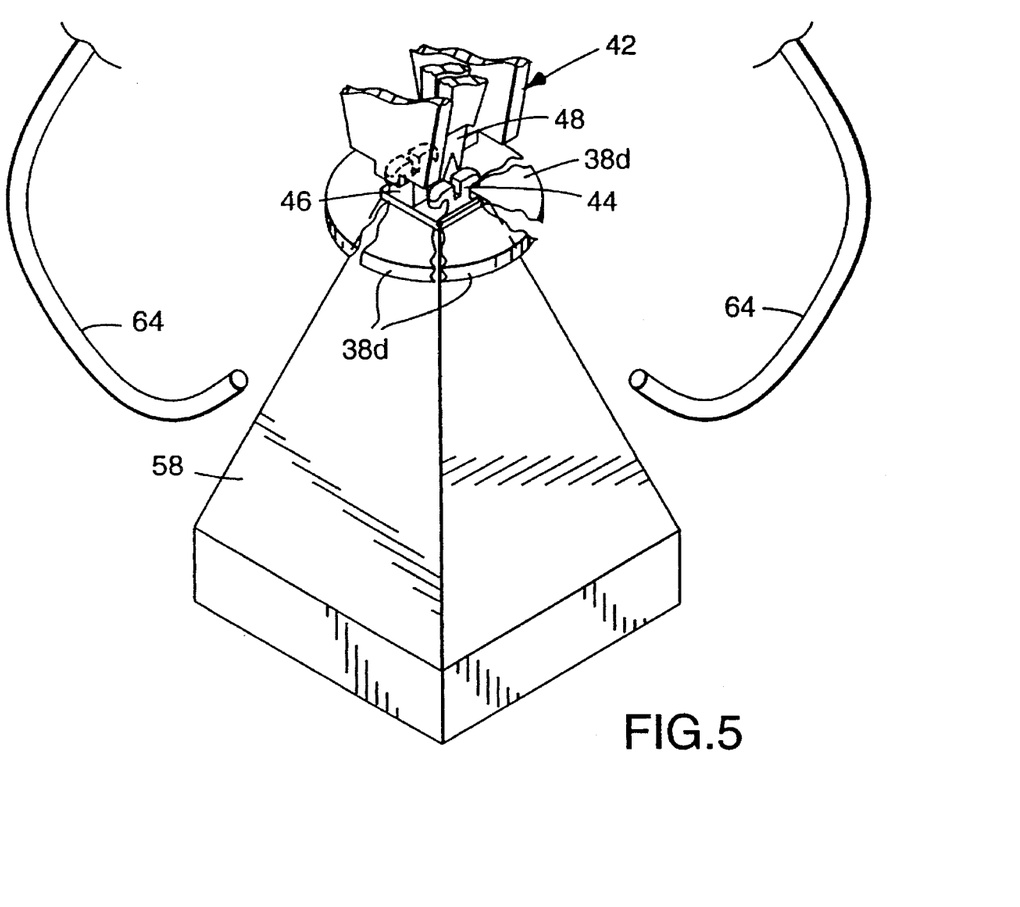
FIG. 5 is an enlarged fragmentary perspective view of a cut-off die that is schematically shown in FIG. 2, wherein the gripper has placed the bracket and the adhesive atop a cutting edge of the die, and wherein nozzles are shown for directing air toward the bracket base in order to blow away excess adhesive.

As illustrated in FIGS. 1 and 3, each of the flattened droplets 38b of adhesive moves toward a location directly over the center of the freezing probe 56 in sequential fashion as the carrier 24 advances. As each droplet 38b moves toward the probe 56, the pick and place device 40 moves the gripper 42 toward the pick-up location 54 on the feeding track 52 to enable the movable fingers 48 to grasp each bracket 44 in serial fashion, and then lift each bracket 44 from the feeding track 52 and carry the bracket 44 toward the freezing probe 56. When each droplet 38b of adhesive reaches a location over the center of the freezing probe 56, advancement of the carrier 24 is interrupted and the gripper 42 descends to push the base of the bracket 44 into the droplet 38b in the manner shown in FIGS. 3–4. Downward movement of the bracket 44 is halted once the distance between the bracket base periphery and the top of the carrier 24 is approximately 0.015 inch (0.4 mm) to 0.02 inch (0.5 mm), depending on the shape of the bracket and desired ultimate thickness of the adhesive.

As each droplet 38b of adhesive moves to the location over the center of the freezing probe 56, and then remains stationery for a short time interval while the bracket 44 is pushed into the droplet 38b, the droplet 38b cools below ambient temperature (i.e., below normal room temperature of about 70° F. or 21° C.). As the droplet 38b is cooled, its elastic modulus is increased. Preferably, a lower portion of the droplet 38b is cooled to a temperature below its glass transition temperature. However, the lower, tooth-facing surface of the base of the bracket 44 is concave in order to match the convex shape of the tooth upon which it is adapted to be mounted. As a consequence, it is preferred that the cooled droplet 38b not be unduly stiff or frozen as the bracket 44 descends, but instead exhibit sufficient fluidity to enable the adhesive of the droplet 38b to flow and easily conform to the concave shape of the bracket base, and in particular to reach the uppermost portion of the concave base surface and to completely cover all portions of the base surface. The freezing probe 56 then continues to cool the adhesive for an additional short time period (e.g., about 1000 milliseconds) and essentially solidifies the adhesive.

Next, the pick and place device 40 moves the gripper 42 upwardly to lift the bracket 44 and the engaged droplet 38b of adhesive from the carrier 24. The droplet 38b readily releases from the carrier 24, inasmuch as cooling of the droplet 38b reduces the tackiness of the adhesive and facilitates release of the adhesive from the carrier 24. Cooling of the droplet 38b also increases its stiffness, such that mechanical retention to the bracket base is enhanced in instances where the base is textured or has undercut recesses.

In practice, satisfactory results have been achieved by setting the temperature controller of the refrigeration unit to −100° F. (−73° C.), although in use the temperature of the freezing probe 56 has been observed only to reach −70 to −80° F. (−57 to −62° C.). The speed of advancement of the carrier 24 and the time cycle of movement of the gripper 42 is such that each droplet 38b is located above the top of the freezing probe 56 for only about 1.0 to 1.25 seconds. Such time is sufficient for the bottom of the droplet 38b to cool to a temperature that facilitates detaching the droplet 38b from the carrier 24, and yet is sufficiently short so that the upper portions of the droplet 38b remain relatively fluid so that the bracket 44 can be easily pushed into the droplet 38b and the adhesive in the droplet 38b readily conforms to the concave surface of the bracket base.

Figure 2:
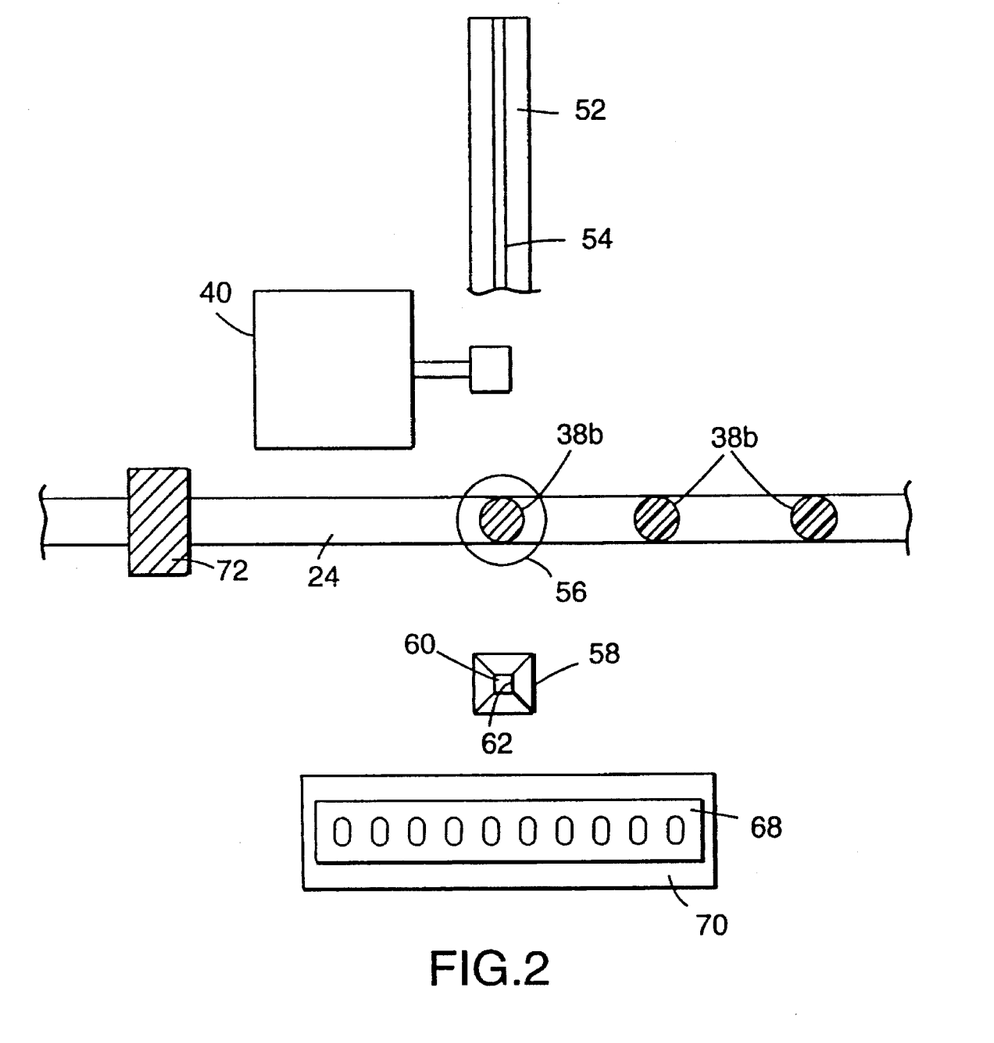
FIG. 2 is a schematic top plan view of a portion of the apparatus shown in FIG. 1 along with additional items not illustrated in FIG. 1.
Figure 6:
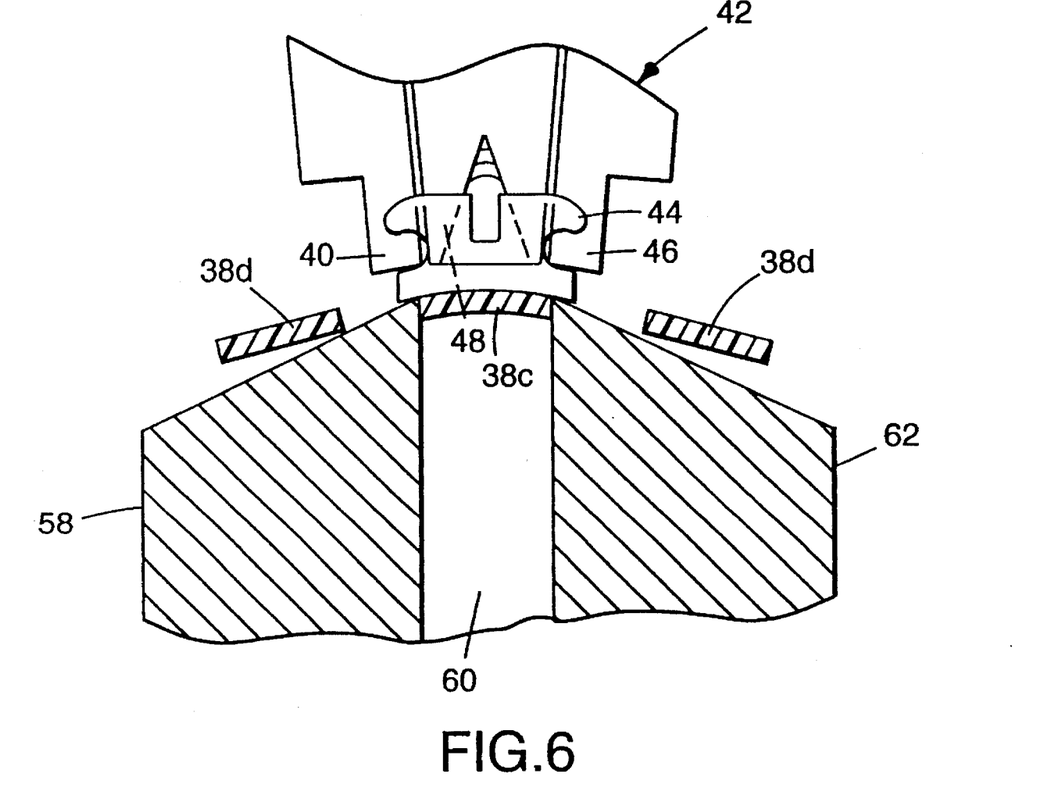
FIG. 6 is a fragmentary, vertical sectional view of the cut-off die, bracket and adhesive shown in FIG. 6, illustrating an interior channel of the die along which air is also directed.
Figure 7:
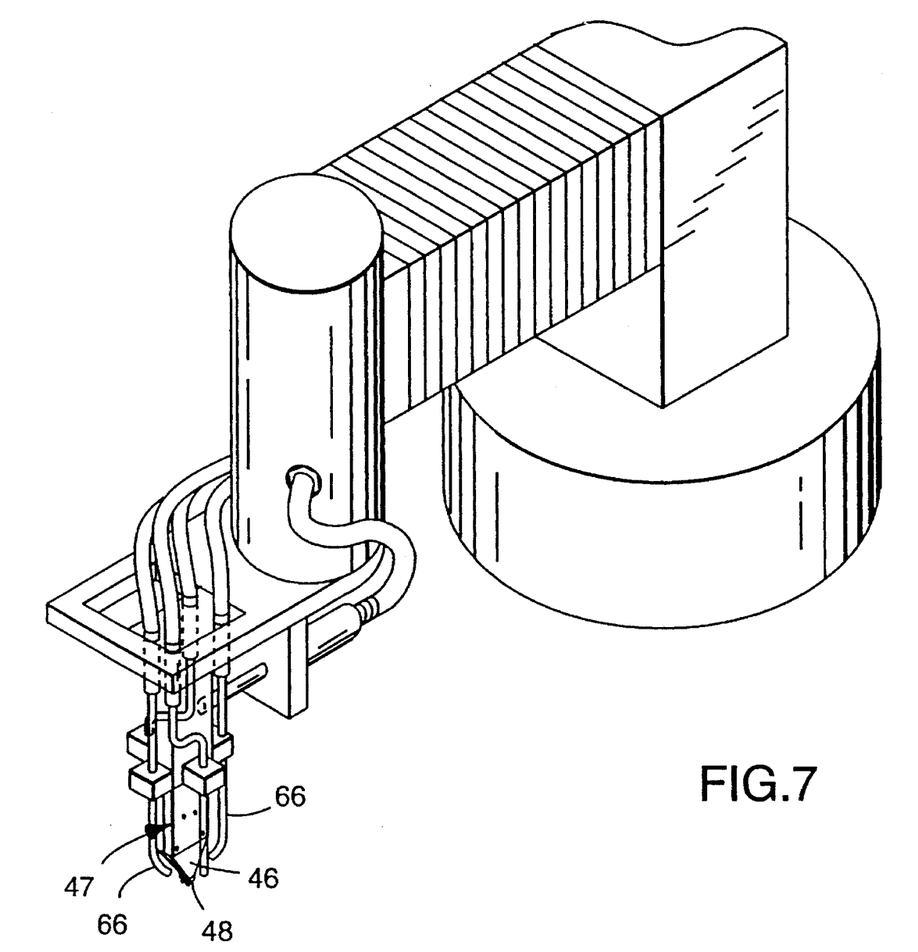
FIG. 7 is a perspective view depicting the pick and place device that is shown schematically in FIGS. 1–2 and is also partially illustrated in FIGS. 3–6.

Subsequently, the gripper 42 moves the bracket 44 horizontally, and then vertically to a polished stainless steel cut-off die 58 (heat treated to 62 Rockwell hardness) that is shown in FIG. 2 and illustrated in more detail in FIGS. 6 and 7. The cut-off die 58 has an upper surface in the general shape of a truncated pyramid, and a central, internal vertical channel 60 (FIG. 7) extends to the top of the cut-off die 58. The top of the cut-off die 58 terminates in a cutting edge 62 that also surrounds the top of the channel 60 and presents a polygonal shape in plan view.

As the bracket 44 descends toward the cutting edge 62 along the central vertical axis of the cut-off die 58, the cutting edge 62 moves into the droplet 38b of adhesive until coming in contact with the concave base surface of the bracket 44, at which time further descent of the bracket 44 is halted. Preferably, the cutting edge 62 has the same general configuration of the perimeter of the base of the bracket 44, but each edge portion of the cutting edge 62 is spaced a distance of 0.02 in. (0.05 mm) inwardly (i.e., toward the center of the bracket base) from the corresponding edge portion of the bracket base. For example, if the perimeter edge of the bracket base is rectangular and has overall dimensions of 0.127×0.102 in. (3.2×2.6 mm), the top of the cutting edge 62 is also rectangular in plan view and has horizontal dimensions of 0.087×0.062 in. (2.2×1.6 mm).

Next, and while the base of the bracket 44 is in contact with the cutting edge 62, a stream of pressurized air is directed upwardly through two stationary air tubes 64 (FIG. 5) that are mounted along two of the four inclined sides of the cut-off die 58. Approximately 0.25 seconds later, a stream of pressurized air begins to flow from each of four tubes 66 that are mounted on the movable arm of the pick and place device 40 surrounding the gripper 42 for movement therewith. (The tubes 66 are shown in FIG. 7, and omitted from the other drawings for purposes of illustration.) The four tubes 66 are arranged to direct pressurized air downwardly along the mesial, distal, occlusal and gingival sides of the bracket 44.

The pressurized air flowing through the tubes 64, 66 breaks away portions of the adhesive droplet that are located outside of the cutting edge 62, and blows the broken away pieces (designated 38d in FIGS. 5–6) away from the bracket 44 and the die 58. Inasmuch as the adhesive droplet when next to the die 58 is still in a cooled state with increased elastic modulus and increased brittleness (as compared to its properties at room temperature), the adhesive droplet behaves as a solid, and the adhesive pieces 38d break relatively cleanly and do not ooze or become stringy as might be observed if trimming of the adhesive was attempted at normal room temperatures. Air continues to flow through the tubes 64, 66 for only a short time as may be necessary to blow away the trimmed adhesive pieces 38d from the base of the bracket 44. In practice, air flow through the tubes 64, 66 is interrupted once the air has passed through the tubes 66 for about 1.2 seconds.

Approximately 0.2 seconds after the flow of air through tubes 64, 66 is interrupted, a stream of pressurized air is directed upwardly through the channel 60 and toward the portion of the adhesive segment (designated 38c in FIG. 6) that is inside the cutting edge 62 and remains affixed to the bracket 44. Next, the pick and place device 40 is actuated to raise the gripper 42 and thus lift the bracket 44 with the adhesive segment 38c away from the cut-off die 58. The stream of pressurized air flowing upwardly through the channel 60 helps to retain the adhesive segment 38c in firm contact with the bracket base as the bracket 44 is lifted from the cutting edge 62, and also assists in clearing the channel 60 of any adhesive fragments that may have unintentionally detached from the adhesive segment 38c (and possibly lodged on the interior side of the cutting edge 62 or the channel 60).

As an option, the use of the cut-off die described above having a cutting edge closely complemental in shape to the perimeter shape of the bracket base may be avoided, by placing the bracket base over a platform that is preferably chilled below ambient temperature to maintain the adhesive in a solid-like condition. The perimeter of the base engages the platform and is used to define a fracture path for the adhesive that is trimmed away from the bracket base. As another option, adhesive trimming is carried out while the adhesive and bracket are located over the freezing probe. However, use of a cutting edge with the precision matched shape as described above reduces the variation in the weight of adhesive that remains affixed to the bracket base, so that more uniform results are achieved from bracket to bracket. As one example, the trimmed adhesive segment weighs about 6.5 mg when the bracket is a 3M Unitek Miniature Twin anterior bracket (3M Unitek, part no. 017-213).

The pick and place device 40 then moves the bracket 44 with the adhesive segment 38c to one of ten wells located in a packaging substrate 68 that is releasably supported by a substrate holder 70. The packaging substrate 68 is made of an opaque flexible material such as black 0.33 mm thick polyethylene terephthalate glycol ("Kodar" brand PETG No. 6763, Kodak Chemical Company) that is treated with a silicone release agent (No. 24, Dow Chemical Company or no. 5M2121, General Electric). The gripper descends toward the substrate 68 until the adhesive segment 38c is received in the well of the substrate 68 and firmly contacts an oval-shaped release liner made of a 0.025 mm thick sheet of clear oriented polyester, type A, that is bonded to the well bottom by an acrylic pressure sensitive adhesive (no. H529; Flexcon). Additional information and alternative constructions of the substrate 68 and the release liner are described in the aforementioned U.S. Pat. No. 5,328,363, which is expressly incorporated by reference herein.

After placing the bracket 44 with the adhesive segment 38c in the well of the packaging substrate 68, the pick and place device 40 moves the gripper 42 back to the pick-up location 54 on the feeding track 52 in order to grasp another bracket 44 and repeat the steps described above. However, the exact path of movement of the gripper 42 will vary somewhat after the bracket 44 is lifted from the cut-off die 58 during each of the ten cycles needed to fill a particular packaging substrate 68, since the ten wells are spaced along the length of the substrate. Once all ten wells of the substrate 68 have received a bracket 44 and adhesive segment 38c, the substrate 68 is removed and receives a lidding that provides a barrier to the transmission of light, water vapor and oxygen. Suitable materials for the lidding include polyester, metallized films, foil and film laminates and other materials such as are described in U.S. Pat. Nos. 5,328,363 and 5,348,154 incorporated by reference herein. Other suitable lidding materials and constructions are described in the paragraphs below in connection with lidding 175. Once assembled, the substrate 68 and the lidding are cut into individual packages (such as the package 185 shown in FIG. 9 and described below).

Incremental movement of the carrier 24 is controlled by the master controller 50 in timed sequence with movement of the gripper 42. As the carrier 24 advances downstream of the freezing probe 56, the carrier 24 passes under a roller 72, and then between the nip of a pair of drive rollers 74, 76 and to a take-up spool 78. The drive rollers 74, 76 are driven by a chain 80 that, in turn, is moved by incremental rotational movement of a servo motor 82 that is operatively connected to the master controller 50.

Figures 8, 9:
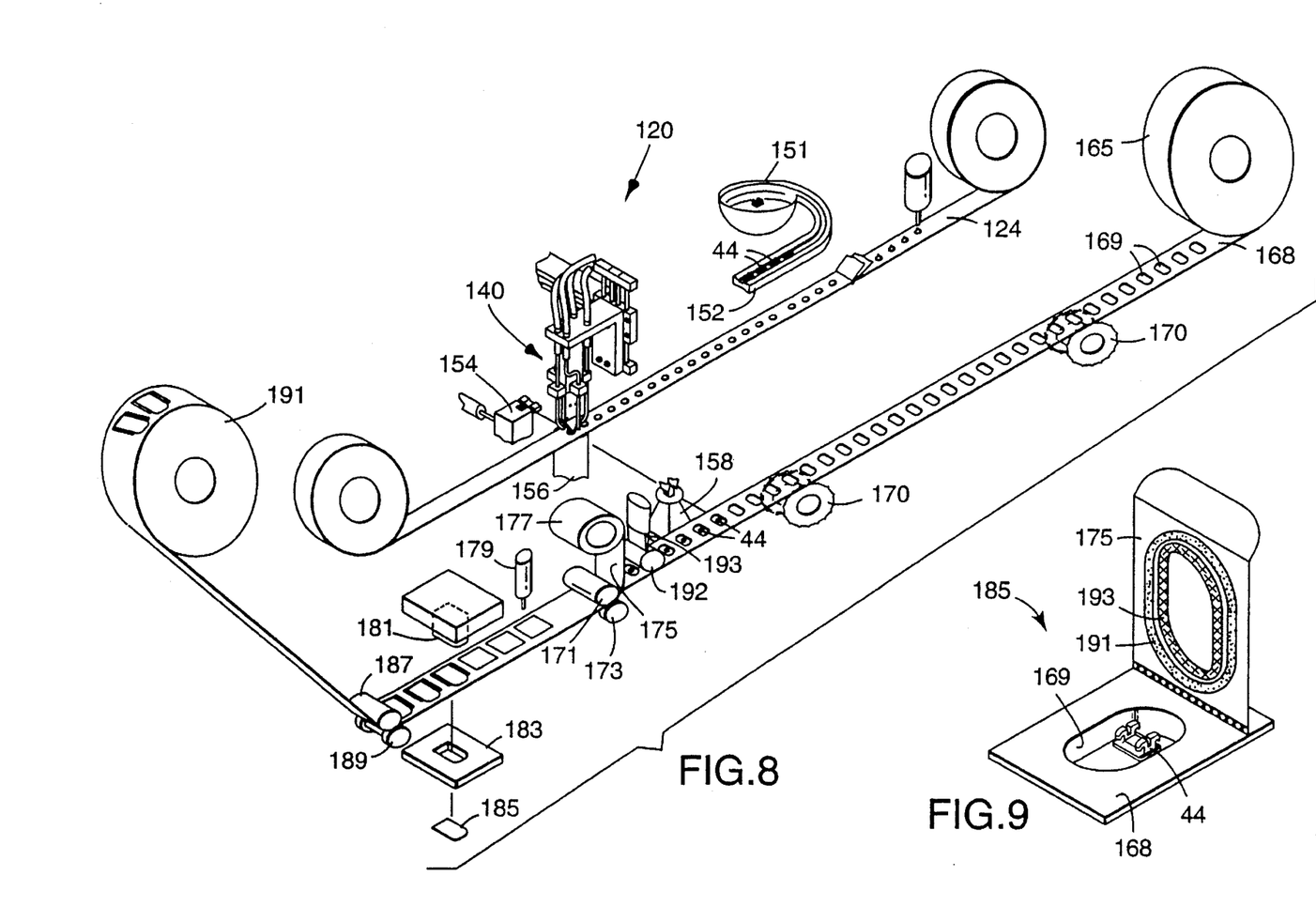
FIG. 8 is a fragmentary perspective view in partially schematic form of apparatus for carrying out a method of the present invention according to another embodiment.
FIG. 9 is an enlarged perspective view of an opened package that was assembled using the apparatus shown in FIG. 8.

FIG. 8 is a schematic view of apparatus 120 that is also useful for applying adhesive to the base of an orthodontic appliance in accordance with another embodiment of the invention. Apparatus 120 includes a vibratory bowl feeder 151 that is operable to position brackets 44 in a common orientation as the brackets 44 are directed in a path along a feeding track 152.

A straight terminal end section of the feeding track 152 (part of which is broken away in FIG. 8) extends in a direction parallel to the direction of advancement of a carrier 124 located alongside the track 152. A movable isolation station 154 is located at the outlet of the feeding track 152 and has an upwardly-facing recess to receive a bracket 44 from the track 152. After the station 154 receives a bracket 44, vibration of the feeding track 152 is interrupted and a pneumatic piston-and-cylinder assembly moves the station 154 laterally of the track 152 to isolate and facilitate pick-up of the bracket 44 by a pick and place device 140. The carrier 124, the pick and place device 140, a freezing probe 156 and a cut-off die 158 are essentially identical to the carrier 24, the pick and place device 40, the freezing probe 56 and the cut-off die 58 respectively described above and as such a further detailed description of such items is unnecessary.

The apparatus 120 includes a reel 165 containing a quantity of packaging substrate 168 made of the materials described earlier in connection with substrate 68. As shown in FIG. 8, the substrate 168 includes a series of spaced apart, oval-shaped wells 169. As an option, a vacuum forming machine may be located downstream of the reel 165 so that wells 169 may be formed in the substrate 168 as the latter is unwound from the reel 165.

The substrate 168 extends in side-by-side, parallel relation to the carrier 124. A series of holes (not shown) are provided along opposite edge portions of the substrate 168 for engagement with driving sprockets 170. Rotational movement of the sprockets 170 is controlled by a master controller to enable the substrate 168 to be advanced in timed, step-wise, synchronous fashion relative to advancement of the carrier 124.

As each flattened adhesive droplet on the carrier 124 approaches a position directly alongside the isolation station 154, the pick and place device 140 moves to pick up a bracket 44 from the station 154, place the bracket 44 in the laterally adjacent adhesive droplet that has been moved by the carrier to a location over the freezing probe 156, and then carry the bracket 44 and the adhesive droplet to the cut-off die 158 where excess adhesive is removed in the manner described earlier in connection with cut-off die 58. Next, the pick and place device 140 places the bracket 44 with its attached, trimmed adhesive segment in the well 169 that has advanced to a position directly adjacent the cut-off die 158.

The substrate 168 is then advanced toward a nip located between a upper cylindrical roller 171 and a lower roller 173, the latter of which has a central recess in order to avoid flattening contact with the wells 169. An elongated strip of lidding 175 is wound about a storage reel 177, and is also fed into the nip between the rollers 171, 173.

The lidding 175 includes a layer of paper that is bonded to a "barrier" layer. The barrier layer is made of aluminum foil or of some other material that substantially blocks passage of the volatile components of the adhesive. The layer of paper faces away from the well 169, while the layer of aluminum foil faces toward the well 169. The layer of paper and layer of aluminum foil are fixed together as a laminate (no. 15113; from Lawson Mardon Flexible, Inc.).

An oval-shaped pressure sensitive adhesive assembly 191 (FIG. 9) releasably connects the lidding 175 to a flange of the substrate 168 surrounding each well 169. Each assembly 191 extends along a first region that at least partially surrounds the opening of the well 169. The adhesive assembly 191 is preferably a laminate that includes a high tack, non-repositionable 0.018–0.02 mm thick layer of acrylic pressure sensitive adhesive (no. H529, Flexcon) that is fixed to the aluminum foil and paper laminate, a 0.018–0.02 mm thick layer of low tack, repositionable acrylic pressure sensitive adhesive (no. H558, Flexcon) that releasably contacts the flange, and a 0.025 mm thick polyester carrier film located between the layer of non-repositionable adhesive and the repositionable adhesive. Each adhesive assembly 191 has an oval-shaped central opening that surrounds the opening of the corresponding well 169.

A hermetic seal connects the lidding 175 to the flange along a second region that surrounds the opening of each well 169. The second region is designated 193 in FIG. 9, although it should be understood in this regard that the hermetic seal is broken when the lidding 175 is opened as depicted in FIG. 9. The second region 193 is located between the first region (where the pressure sensitive adhesive assembly 191 releasably connects the lidding 175 to the flange) and the opening to each well 169. The hermetic seal substantially prevents at least a portion of volatile components of the adhesive on the bracket 44 from contacting the adhesive assembly 191 and extends the shelf life of the packaged adhesive.

A layer of hot melt adhesive extends along the underside surface of the aluminum foil layer. The hermetic seal is made by pressing a heated, annular, oval-shaped face of a platen (not shown) onto the paper and aluminum foil laminate along the second region 193. As the platen presses the paper and aluminum foil laminate into firm contact with the flange of the substrate 168 within the oval-shaped opening of the pressure sensitive adhesive assembly 191, the hot melt adhesive is softened. Subsequently, the platen is moved away from the paper and aluminum foil laminate to enable the hot melt adhesive to cool and thereafter mechanically fix as well as hermetically seal the aluminum foil to the flange.

When the lidding 175 is moved to its open orientation as shown in FIG. 9, the hermetic seal ruptures, and the repositionable adhesive of the pressure sensitive adhesive assembly 19 1 detaches from the flange. If desired, the lidding 175 may subsequently be reclosed by moving the lidding downward in an arc so that the repositionable adhesive again contacts the flange to thereafter retain the lidding 175 in its closed orientation.

Other suitable liddings and packages are described in U.S. Pat. No. 5,015,180 and 5,328,363 and copending U.S. patent application Ser. No. 08/407,190 entitled "Package for Adhesive Precoated Dental Appliance" filed on even date herewith. An another option, the lidding 175 may be releasably connected to the substrate 168 by a liquid pressure sensitive adhesive that has been applied to the top surface of the substrate 168 by a sponge roller. The sponge roller is not shown in the drawings, but is located immediately upstream of the rollers 171, 173. A jet sprayer or other device supplies the liquid pressure sensitive adhesive to the sponge roller to maintain the latter in a wetted condition at all times.

Preferably, a top layer is joined to the lidding 175 to provide rigidity and stiffness and also to present a printable top surface. A preferred top layer is made of a 0.13 mm thick opaque white polyester film (Melanex no. 329; from ICI) that is secured to the lidding 175 by a 0.025 mm thick layer of pressure sensitive adhesive (Scotch no. 9447 laminating adhesive; from 3M). The top layer is affixed to the lidding 175 after the heat sealing operation is completed, and the top layer has the same shape as the shape of the lidding 175.

The platen also includes a heated rectangular face that engages a rear section of the lidding 175 when the oval-shaped platen face contacts the lidding 175. The rear section is located rearwardly of the pressure sensitive assembly 191, and is heat-sealed by the rectangular face of the platen to an underlying, similarly-shaped section of the flange to help insure that the lidding 175 and the top layer do not completely detach from the flange when the lidding 175 and the top layer are opened.

For the heat sealing operation, the flange is preferably placed upon an aluminum pad or a resilient pad (such as a 70 durometer 0.03 in. (0.8 mm) thick silicone rubber pad) to provide support for the substrate 168. Although not shown, the support pad could be mounted on a movable arm that retracts as the substrate 168 is advanced. The platen temperature, the pressure of the platen against the lidding 175 and time interval that the platen is held under pressure against the lidding 175 are parameters that can be varied as may be needed to establish a satisfactory hermetic seal. As an example, the platen temperature may be about 365° F. (185° C.) when held against a section of the lidding 175 extending over ten wells 169 for about 2–3 seconds and with a pressure of about 500 lbs. (227 kg). As another example, the platen temperature may be about 80° C. and held against the lidding 175 with a pressure of about 1.5 to 2.0 kg/cm².

The lidding 175 and the top layer include a line of perforations that extends across the rear section of the lidding 175. When the lidding 175 and top layer are moved to an open, upstanding position, the lidding 175 and the top layer bend at the perforations in order to facilitate self-retention of the lidding 175 and the top layer in their open, upright position. The perforations also provide tactile feedback to the user that the lidding 175 and top layer are open so that user does not continue to pull on the lidding 175 and top layer and separate the same from the substrate 168.

Optionally, one or more of the perforations is replaced with a staked connection wherein an elongated portion of the lidding 175 and the top layer are firmly pressed into an underlying portion of the flange to establish a mechanical interlock. The staked connection further helps insure that the lidding 175 and the top layer do not completely detach from the flange when the lidding 175 and the top layer are opened.

An ink-jet printer 179, controlled in synchronous fashion by the master controller controlling advancement of the substrate 168, is located downstream of rollers 171, 173 and the platen. The printer 179 provides indicia on the lidding 175 that identifies the lot number and the type of bracket 44 carried in the underlying well 169.

Next, the lidding 175 and the substrate 168 are advanced to a die cutting station, where a punch 18 1 (that is controlled by the master controller) is lowered toward a die 183 to cut both the lidding 175 and the substrate 168 and make an individual package 185 containing a single bracket 44. Preferably, the sprocket drive holes located in the edge portions of the substrate 168 are not located directly next to the wells 169, and the lidding 175 is wider than the substrate 168, so that a section of the cut lidding 175 overhangs the cut substrate 168 to form a finger-grippable tab for opening the package 185 when desired.

Although not shown in the drawings, a second pick and place device may optionally be used to retrieve the package 185 and place the latter in a storage or shipping container. The package 185 is shown alone in FIG. 9 as it appears during opening and is described in more detail in pending U.S. patent application Ser. Nos. 08/052,334, now U.S. Pat. No. 5,328,363 and 08/071,037, now U.S. Pat. No. 5,348, 154. The remaining portions of the substrate 168 and lidding 175 pass through a nip between a second pair of rollers 187, 189 and to a take-up reel 191.

Figure 10:
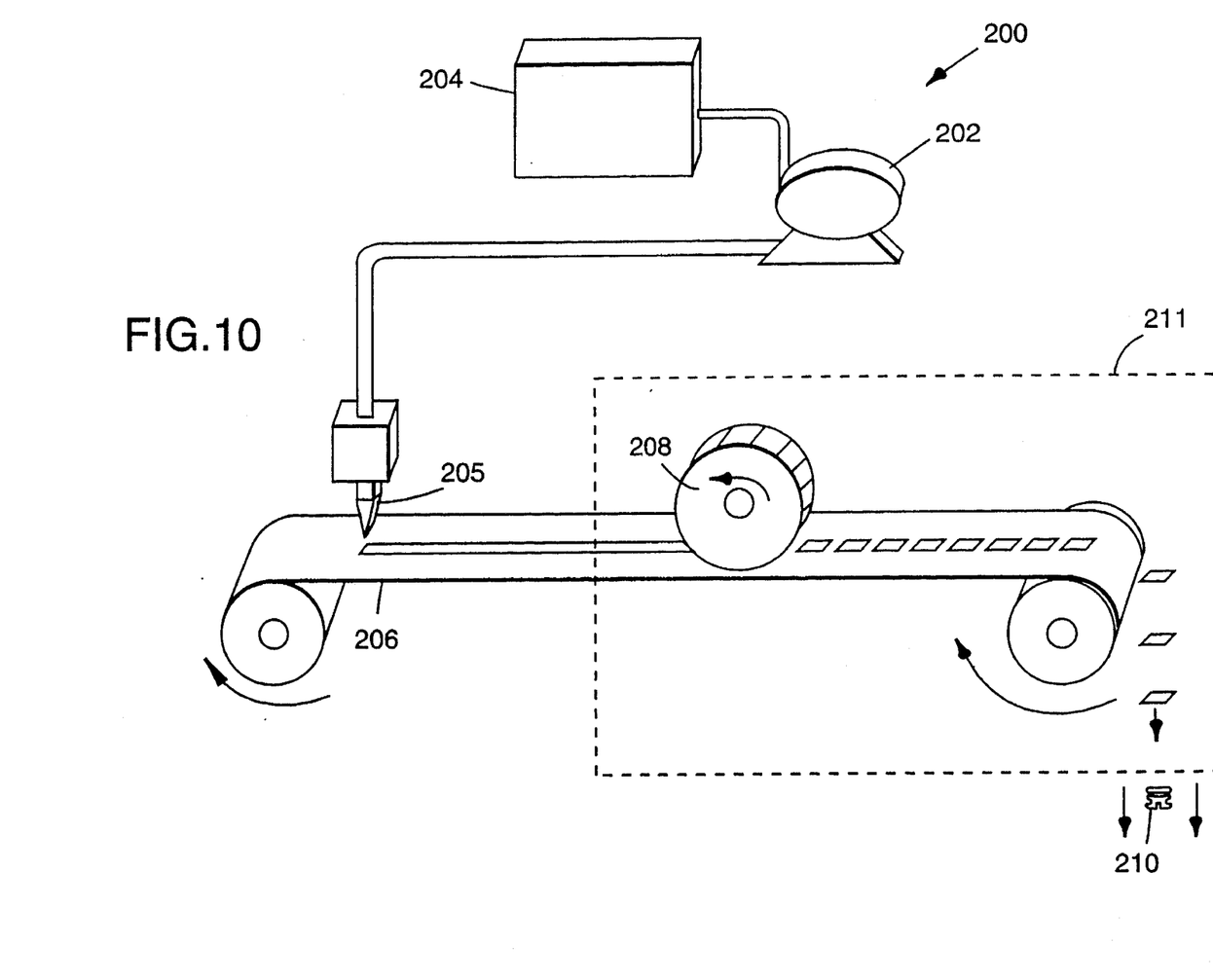
FIG. 10 is a vertical schematic view of apparatus for carrying out a method of the present invention according to yet another embodiment.

The embodiment of the invention that is schematically described in FIG. 10 concerns another method of applying adhesive to the base of an orthodontic appliance that, in this instance, is carried out by apparatus 200. The apparatus 200 includes a positive displacement or high pressure pump 202 (that is optionally similar to dispensing unit 36 described above) capable of pumping heavy body liquids or pastes. The pump 202 dispenses adhesive from a pressurized reservoir 204 through a nozzle 205 retained at ambient temperature or at a temperature somewhat above ambient. Adhesive is dispensed in the form of a continuous strip from the nozzle 205 onto a moving, endless loop carrier belt 206. Alternatively, the carrier belt 206 could be roll stock of releasable web that is continuously unwound as a carrier and then taken up after cut sections of adhesive are removed from the web.

The carrier belt 206 is made of, or has an external surface of, a material that readily releases from the adhesive, such as polyester or polytetrafluoroethylene. As the carrier belt 206 is advanced in the direction shown by the arrows, the strip of adhesive moves into a cold zone 211 wherein the temperature is maintained below ambient temperature, and preferably less than 5° C. The cold zone 211 could be a chamber, room, or an area adjacent a freezing probe or cold stream of gas (such as nitrogen). The adhesive cools in the cold zone 211 to a temperature below its glass transition temperature, and is cut into sections by knife edges of a rotary blade cutter 208 (or alternatively by a guillotine knife).

Preferably, the rotary cutter is constructed so that the cut adhesive sections match the configuration of the bracket base. The shape of the outlet opening of the nozzle 205, the extrusion rate of the adhesive from the nozzle 205 and the speed of the carrier belt 205 control the initial cross-sectional area and shape, and hence the weight of adhesive per unit length, while the rotary cutter controls the length.

Next, a pick and place device with grips located in the cold zone 211 (not shown, but similar to the pick and place device 40 described above) is moved by a computer to serially grasp the cut sections of adhesive. Each section is placed onto the base of a bracket 210 that is held in an inverted position with the base of the bracket facing upwardly. As alternatives, the pick and place device could be used to carry the brackets to the cut sections of adhesive in the cold zone 211, or a moving carrier belt could carry a sequence of brackets next to the carrier belt 206.

Once the adhesive section is firmly seated on the bracket base, the adhesive is allowed to warm to ambient temperature or higher (up to 70° C.) to enable the adhesive to flow into the texture of the bracket base and wet the base. If desired, the brackets may be preheated in order to facilitate the melting and penetration of the adhesive into the texture or any undercut recesses of the bracket base. The bracket and the attached adhesive section are then placed into a package such as the package 185 described above.

As can be appreciated by the embodiments set out above, the present invention is advantageous in that handling of the adhesive is facilitated by cooling the adhesive below ambient temperature. Cooling of the adhesive not only facilitates cutting the adhesive into separate sections, but also eases handling of the adhesive when coating the bracket, as the adhesive at room temperatures is more tacky. Moreover, the shape of the adhesive section can be relatively precisely controlled, so that the manufacturer can insure that the amount of adhesive applied to each bracket is within certain controlled, precise tolerances.

The methods of the invention as set out above also take advantage of the improved flow characteristics of the adhesive when the adhesive is at ambient conditions or warmed to a temperature above ambient. For example, dispensing of the adhesive onto the carrier is facilitated by dispensing the adhesive at room temperature or at a temperature above ambient. Additionally, in the embodiment described in connection with FIG. 10 hereinabove, contact of the adhesive section with the bracket base is facilitated by heating the bracket base to warm the adhesive.

Those skilled in the art will recognize that other modifications, additions or alternatives are possible without departing from the spirit of our invention. For example, a variety of other packages or containers could be used, such as those described in U.S. Pat. Nos. 5,015,180 and 5,328,363 and copending U.S. patent application Ser. No. 08/407,190 entitled "Package for Adhesive Precoated Dental Appliance" filed on even date herewith. Accordingly, the invention should not be deemed limited by the specific embodiments set out above, but instead only by a fair scope of the claims that follow along with their equivalents.

We claim:

1. A method for applying adhesive to a base of an orthodontic appliance comprising the steps of:

placing a quantity of adhesive onto a carrier;

maintaining at least a portion of the adhesive on the carrier at a temperature below room temperature;

contacting the base of the appliance with the adhesive; and disengaging the adhesive from the carder while the temperature of the portion of the adhesive is below room temperature.

2. The method of claim 1 including the step of relatively moving the appliance and the carrier away from each other to disengage the adhesive from the carrier while the adhesive is in contact with the appliance.

3. The method of claim 1 wherein said step of placing the quantity of adhesive onto a carrier includes the step of placing a discrete quantity of adhesive on the carrier in spaced relation to other discrete quantities of adhesive on the carrier.

4. The method of claim 1, further including the step of pressing the adhesive before said step of contacting the base of the appliance with the adhesive.

5. The method of claim 1, further including the step of trimming excessive adhesive from the appliance while the temperature of the portion of the adhesive remains below room temperature.

6. The method of claim 5, wherein said step of trimming the adhesive includes the step of directing a stream of pressurized air toward the base of the appliance.

7. The method of claim 6, wherein said step of trimming the adhesive further includes placing the base of the appliance over a cutting edge.

8. The method of claim 7, wherein said appliance base has a perimeter, and wherein said step of placing the appliance over the cutting edge further includes the step of moving the cutting edge toward a location on the appliance base spaced inwardly from the perimeter of the appliance base.

9. The method of claim 1, further including the step of warming the adhesive before said step of placing the quantity of adhesive onto the carrier.

10. The method of claim 1, further including the step of warming the appliance to a temperature above room temperature.

11. The method of claim 1, further including the step of cutting the adhesive into sections while the adhesive is maintained at a temperature below room temperature.

12. The method of claim 1, further including the step of pressing the adhesive while the adhesive is on the carrier.

13. The method of claim 1, wherein said step of contacting the base of the appliance with the adhesive is carried out while the temperature of the adhesive is below room temperature and after said step of disengaging the adhesive from the carrier.

14. The method of claim 1, wherein said step of maintaining at least a portion of the adhesive on the carrier at a temperature below room temperature is carried out using a cooling probe.

15. The method of claim 1, wherein said step of maintaining at least a portion of the adhesive on the carrier at a temperature below room temperature is carded out in a chamber having a cold zone.

* * * * *

UNITED STATES PATENT AND TRADEMARK OFFICE
CERTIFICATE OF CORRECTION

PATENT NO.: 5,552,177

DATED: 9-3-96

INVENTOR(S): Dwight W. Jacobs, Oliver L. Puttler, Evangelos G. Georgakis, Allen B. Amundson and Russell A. Jordan It is certified that error appears in the above-identified patent and that said Letters Patent is hereby corrected as shown below:

Col. 13, line 27, "carder" should read -- carrier --.

Col. 14, line 38, "carded" should read -- carried --.

Signed and Sealed this

Twenty-third Day of September, 1997

Attest:

BRUCE LEHMAN

Attesting Officer

Commissioner of Patents and Trademarks